United States Patent
Chung et al.

(10) Patent No.: US 10,351,598 B2
(45) Date of Patent: Jul. 16, 2019

(54) PEPTIDE WITH ANTI-OBESITY AND ANTI-DIABETIC EFFICACY AND USE THEREOF

(71) Applicant: CAREGEN CO., LTD., Anyang-si (KR)

(72) Inventors: Yong Ji Chung, Yongin-si (KR); Eun Mi Kim, Yongin-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 16/091,791

(22) PCT Filed: Mar. 17, 2017

(86) PCT No.: PCT/KR2017/002884
§ 371 (c)(1),
(2) Date: Oct. 5, 2018

(87) PCT Pub. No.: WO2017/179824
PCT Pub. Date: Oct. 19, 2017

(65) Prior Publication Data
US 2019/0100556 A1 Apr. 4, 2019

(30) Foreign Application Priority Data
Apr. 15, 2016 (KR) .......................... 10-2016-0046097

(51) Int. Cl.
| | |
|---|---|
| *A61K 38/08* | (2019.01) |
| *A61K 38/00* | (2006.01) |
| *C07K 7/06* | (2006.01) |
| *C07K 7/00* | (2006.01) |
| *A61P 3/10* | (2006.01) |

(52) U.S. Cl.
CPC ................ *C07K 7/06* (2013.01); *A61K 38/08* (2013.01); *A61P 3/10* (2018.01); *A61K 38/00* (2013.01)

(58) Field of Classification Search
CPC .......... A61K 38/08; A61K 38/00; C07K 7/06; C07K 7/00
USPC ................... 514/6.9, 21.8, 1.1; 530/330, 300
See application file for complete search history.

(56) References Cited

U.S. PATENT DOCUMENTS

| | | | |
|---|---|---|---|
| 6,617,156 B1* | 9/2003 | Doucette-Stamm | ........................ C07K 14/315 435/252.3 |
| 9,278,067 B2* | 3/2016 | Boulikas | .............. A61K 9/1271 |
| 2007/0275872 A1 | 11/2007 | Cooper et al. | |
| 2012/0029065 A1 | 2/2012 | Sinclair et al. | |
| 2016/0002303 A1 | 1/2016 | Montserrat Carreras et al. | |
| 2018/0118783 A1 | 5/2018 | Chung et al. | |

FOREIGN PATENT DOCUMENTS

| | | |
|---|---|---|
| JP | 2013-035867 A | 2/2013 |
| JP | 2016-508510 A | 3/2016 |
| KR | 101063895 B1 | 9/2011 |
| KR | 10-2014-0027594 A | 3/2014 |
| KR | 101669140 B1 | 10/2016 |

OTHER PUBLICATIONS

Q660U6 from UniProt, pp. 1-3. Integrated into UniProtKB/TrEMBL on Oct. 11, 2004.*
A0A0S2DNR6 from UniProt, pp. 1-3. Integrated into UniProtKB/TrEMBL on Feb. 17, 2016.*
Extended European Search Report dated Mar. 21, 2019 for European Patent Application No. 17782579.1, Chung et al., "Peptide with Anti-Obesity and Anti-Diabetic Efficacy and Use Thereof," filed Mar. 17, 2017 (5 pages).
Narayan et al., "A multiprotein binding interface in an intrinsically disordered region of the tumor suppressor protein interferon regulatory factor-1," J Biol Chem. 286(16):14291-303 (including supplement) (2011) (18 pages).
Tomas et al., "GLP-1(32-36)amide Pentapeptide Increases Basal Energy Expenditure and Inhibits Weight Gain in Obese Mice," Diabetes. 64(7):2409-19 (2015).
International Search Report dated Jul. 17, 2017 for International Patent Application No. PCT/KR2017/002884, Chung et al., "Peptide with Anti-Obesity and Anti-Diabetic Efficacy and Use Thereof," filed Mar. 17, 2017 (6 pages).

* cited by examiner

*Primary Examiner* — Julie Ha
(74) *Attorney, Agent, or Firm* — Clark & Elbing LLP; Susan M. Michaud

(57) ABSTRACT

The present invention provides peptides with an anti-obesity and/or anti-diabetic activity consisting of an amino acid sequence of SEQ ID NO: 1 or SEQ ID NO: 2, and optionally modified at their C- or N-terminal ends.

15 Claims, 18 Drawing Sheets
Specification includes a Sequence Listing.

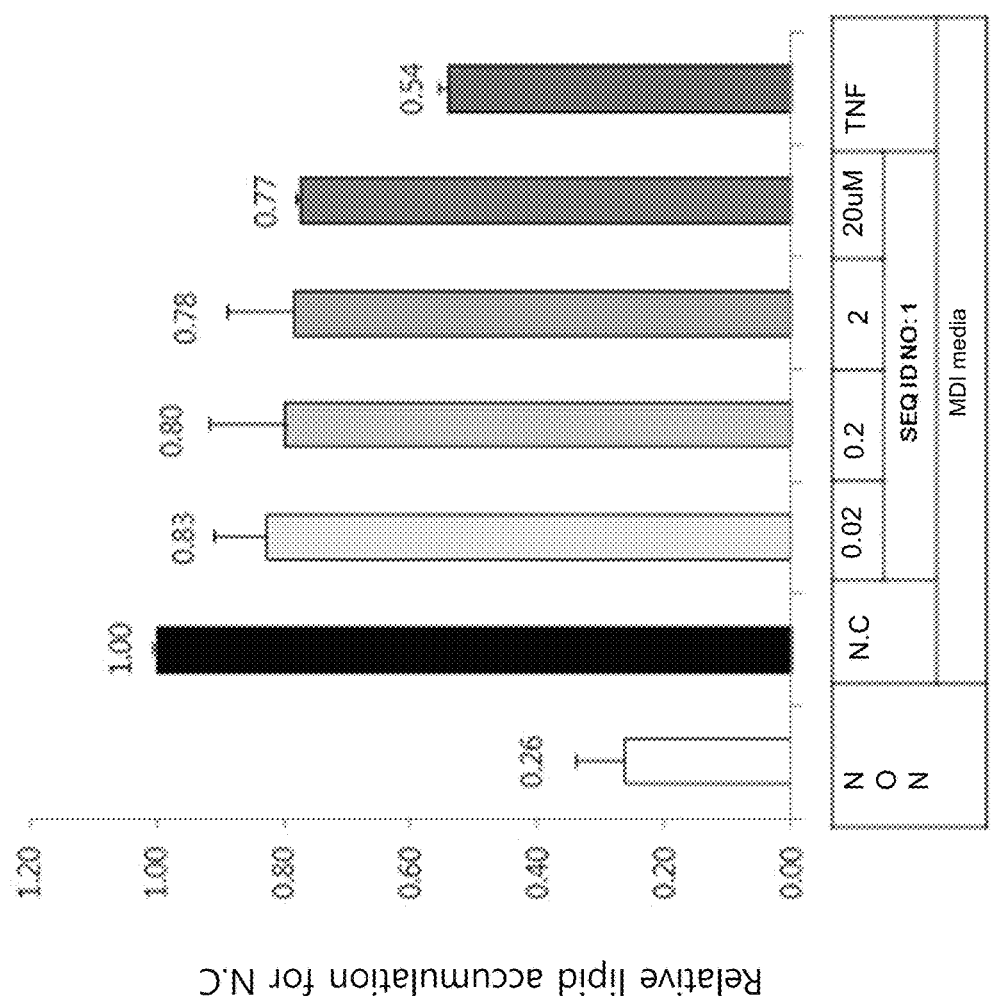

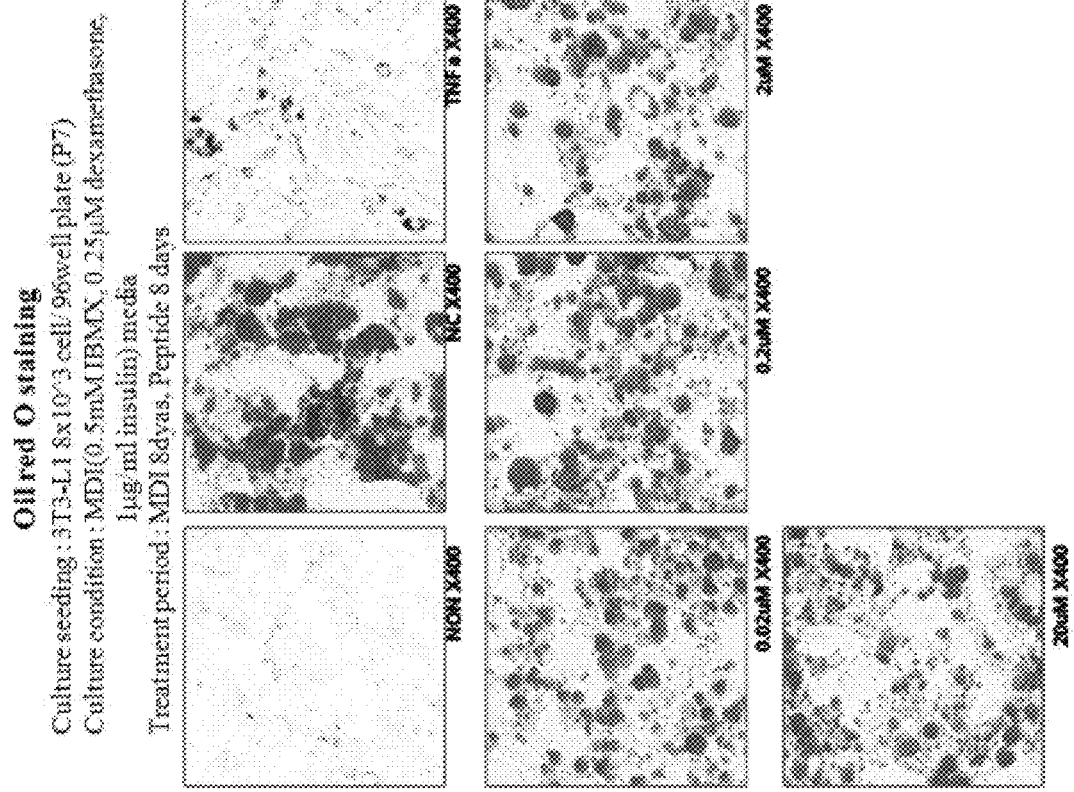

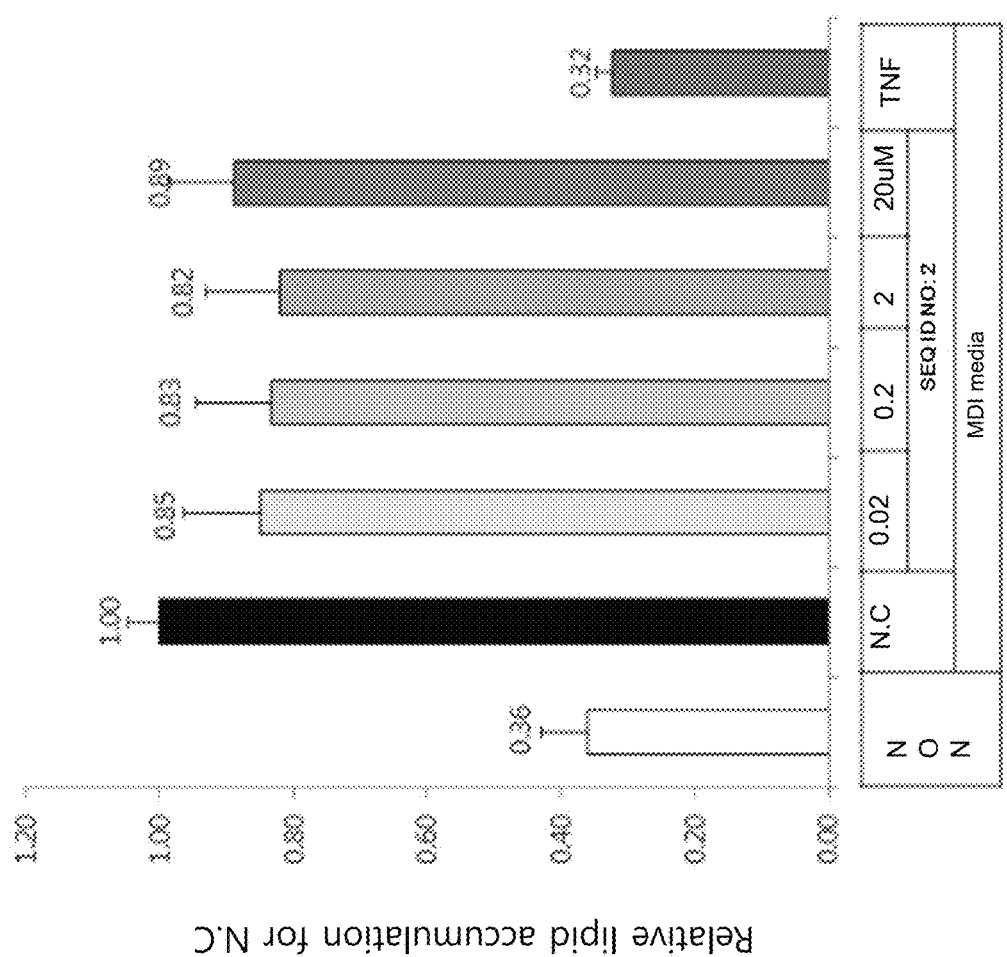

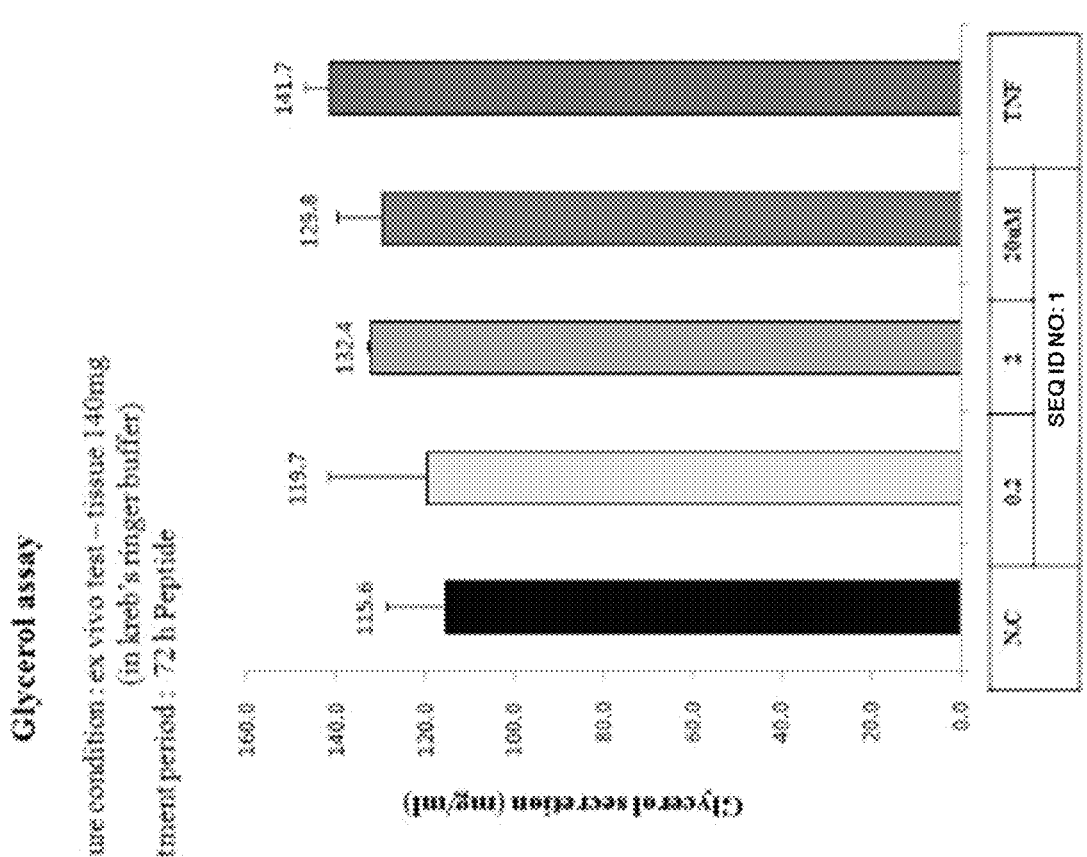

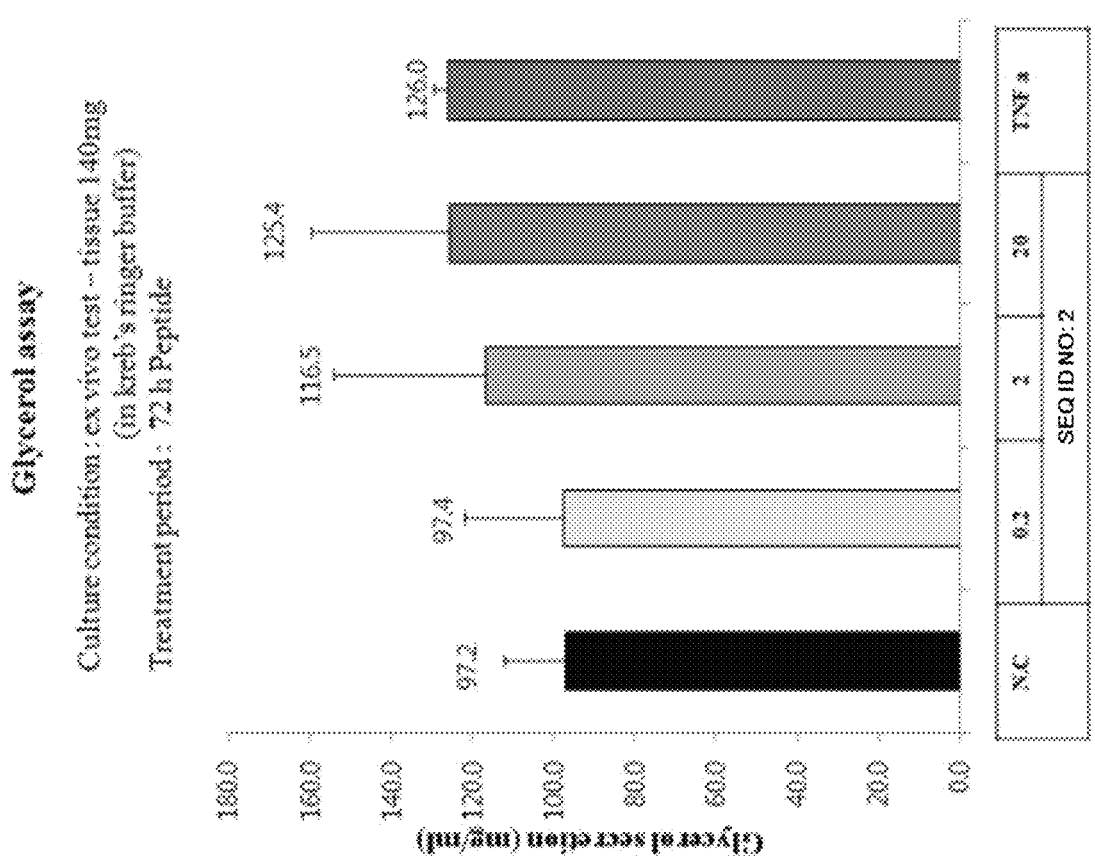

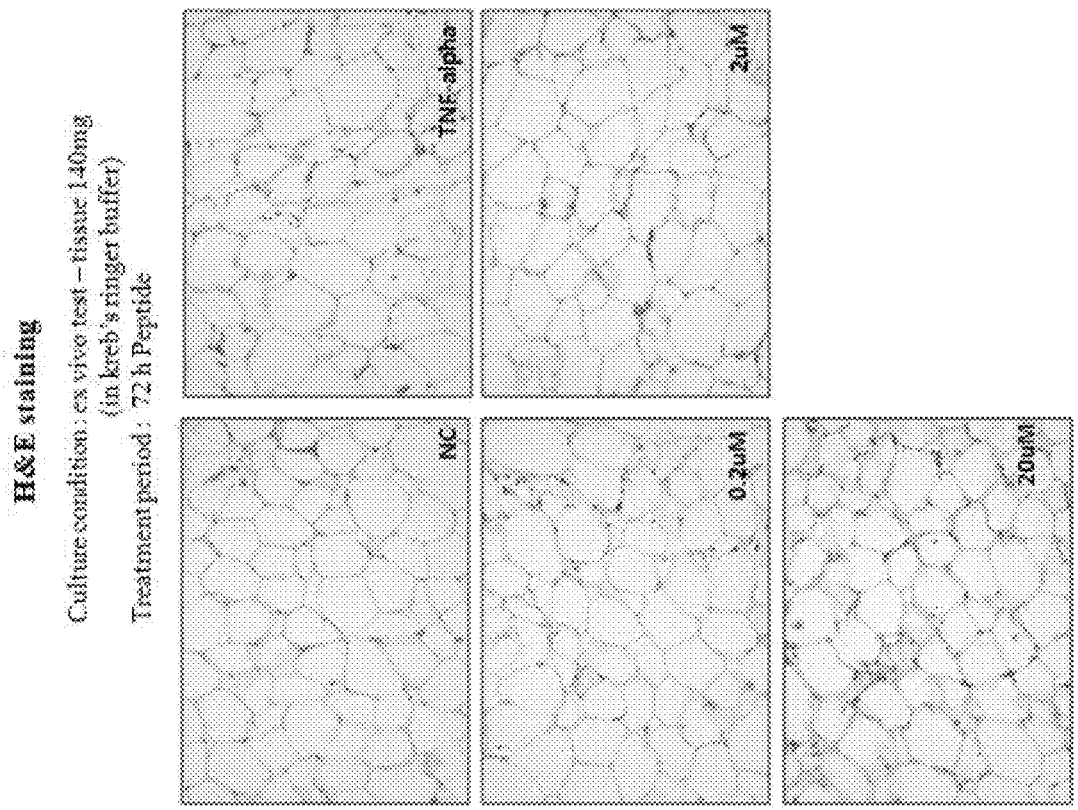

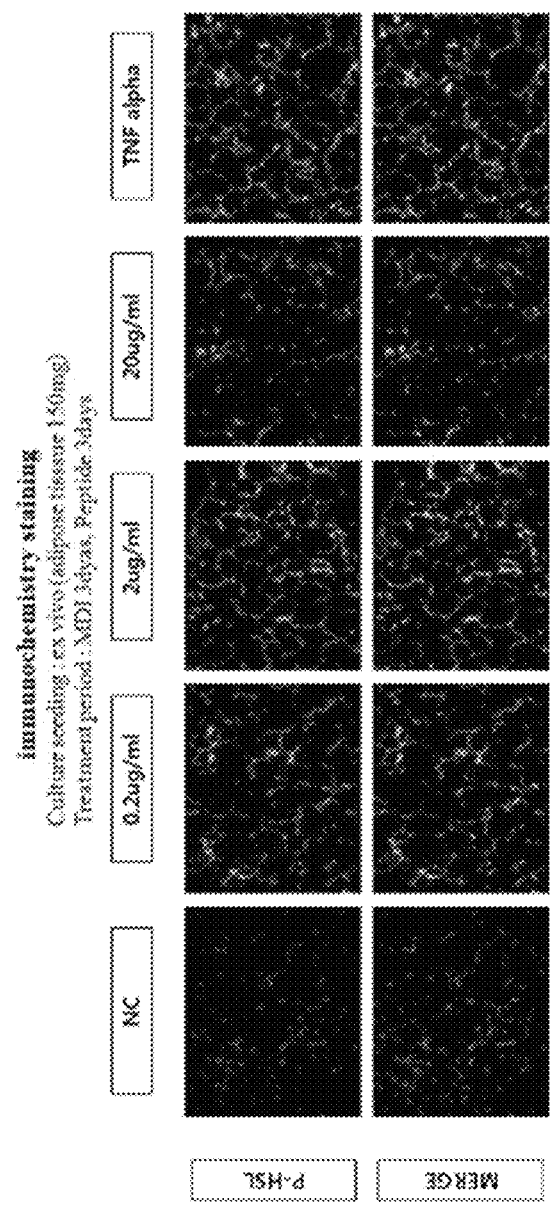

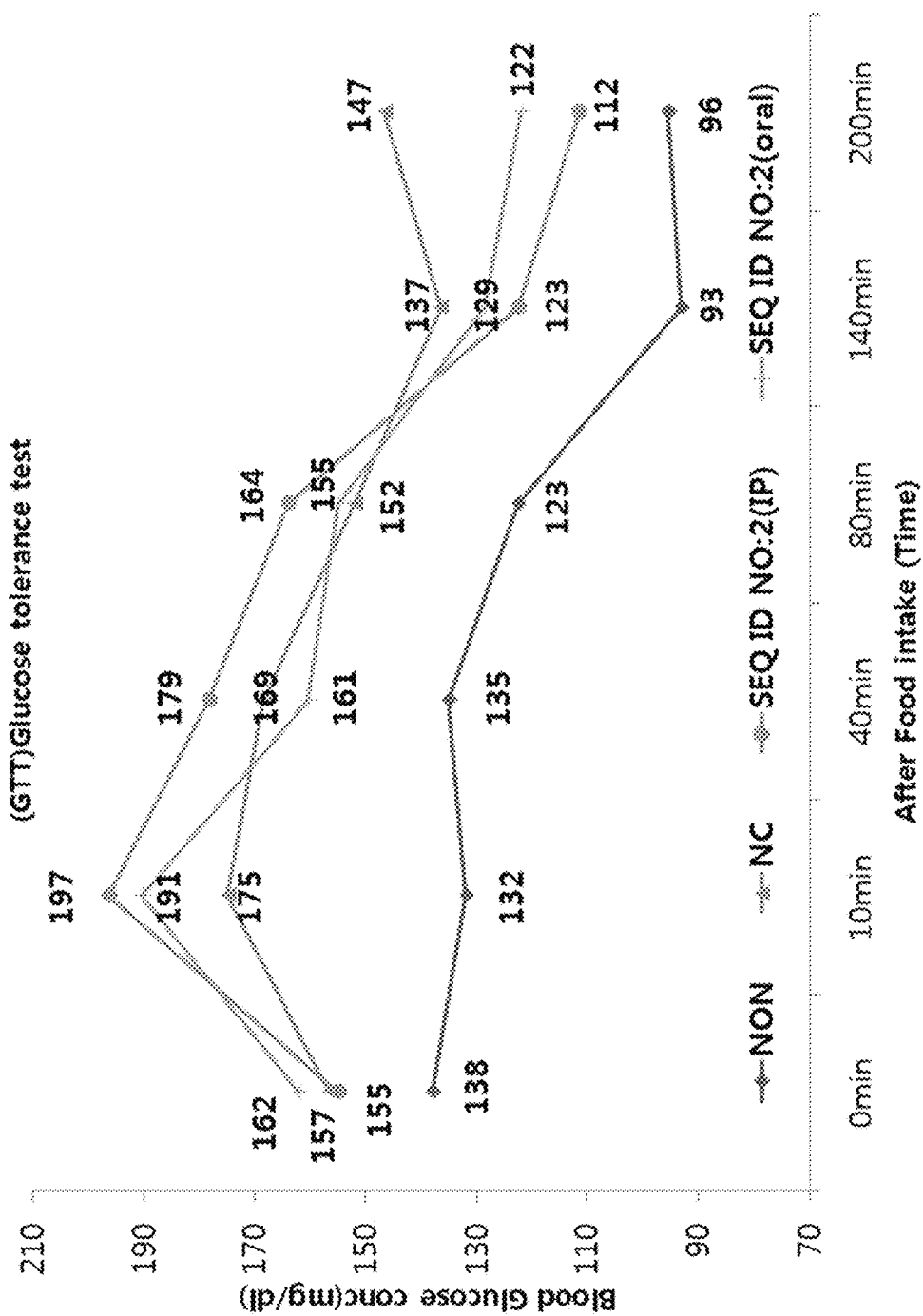

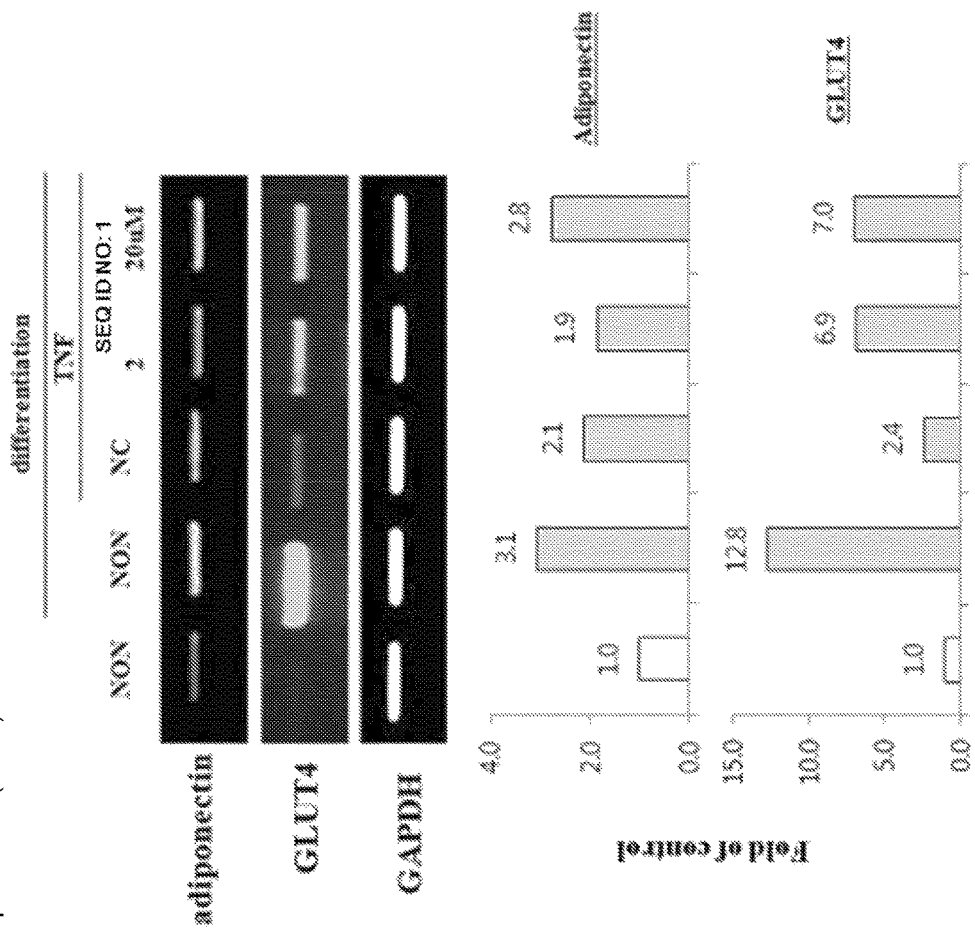

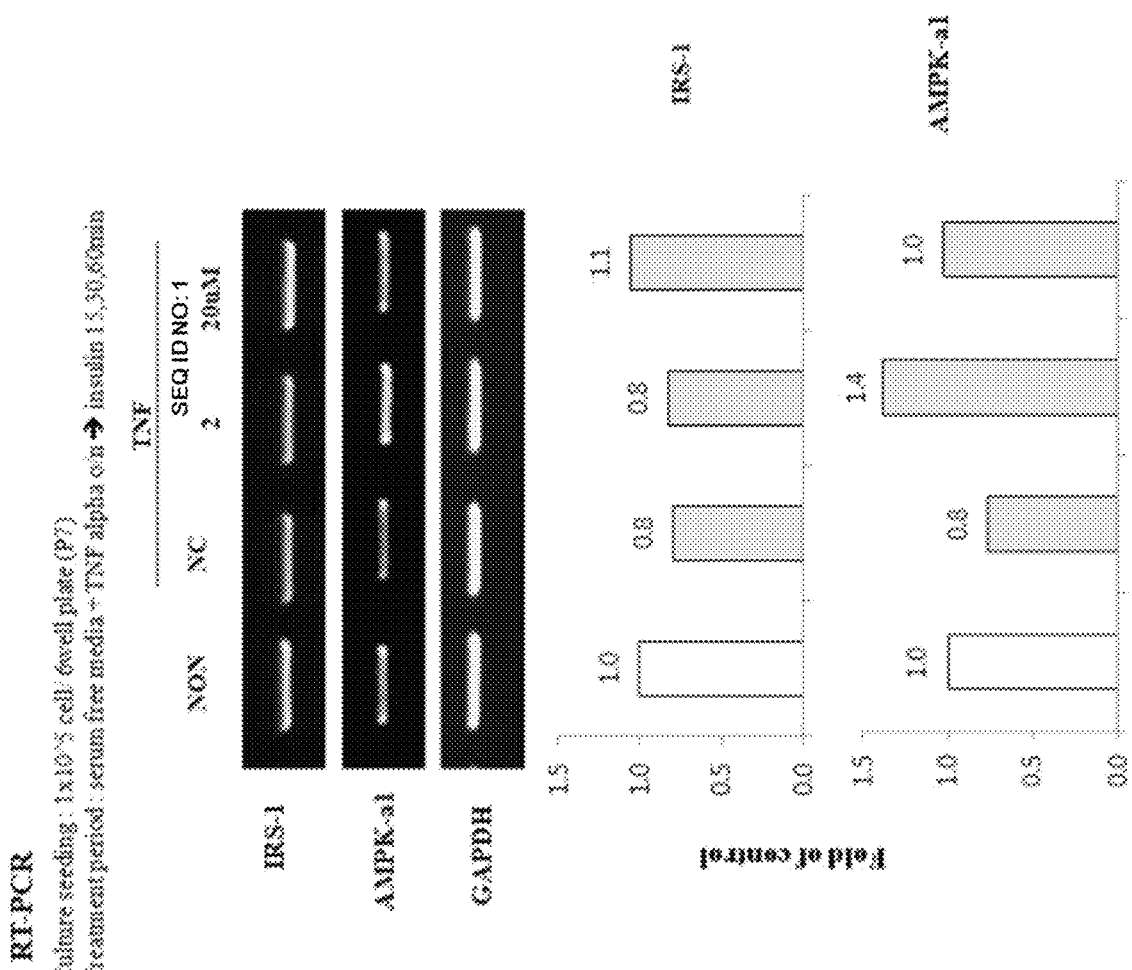

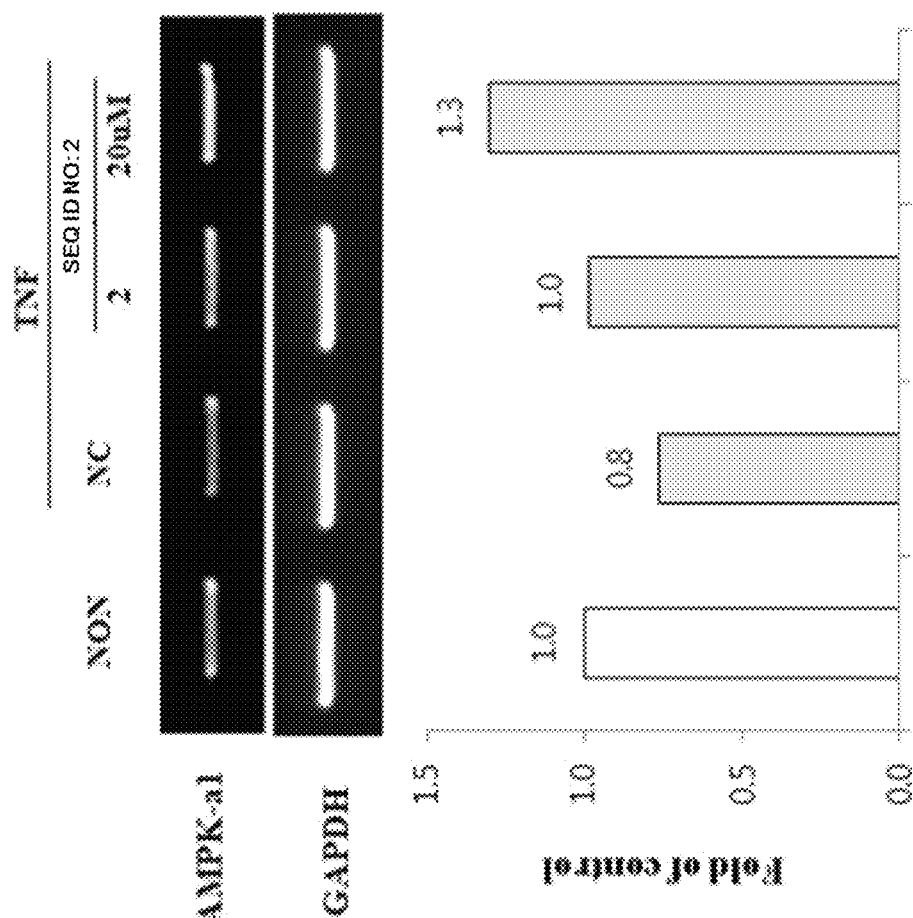

```
                            SEQUENCE LISTING

<160> NUMBER OF SEQ ID NOS: 12

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Lys Glu Arg Lys Ser
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

His Glu Thr Phe Glu
1               5

<210> SEQ ID NO 3
<211> LENGTH: 24
<212> TYPE: DNA
<213> ORGANISM: Artificial Sequence
<220> FEATURE:
<223> OTHER INFORMATION: Synthetic Construct

<400> SEQUENCE: 3
tgtgcaggac tcttacttgg cagt                                              24

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct

<400> SEQUENCE: 4
gtttctttgg gcagaccggt ttct                                              24

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
gccaatcttc atccagttgc                                                   20

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
```

```
catcgtgaag aaggcatagg                                                    20

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
aagatggcca cggagagag                                                     19

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
gtgggttgtg gcagtgagtc                                                    20

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
gccaatcttc atccagttgc                                                    20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
catcgtgaag aaggcatagg                                                    20

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct

<400> SEQUENCE: 11
tgaccggaca taaagtggct gtga                                               24

<210> SEQ ID NO 12
<211> LENGTH: 24
<212> TYPE: DNA
<213> ORGANISM: Artificial Sequence
<220> FEATURE:
<223> OTHER INFORMATION: Synthetic Construct

<400> SEQUENCE: 12
tgatgatgtg agggtgcctg aaca                                               24
```

PEPTIDE WITH ANTI-OBESITY AND ANTI-DIABETIC EFFICACY AND USE THEREOF

TECHNICAL FIELD

The present invention relates to a peptide having anti-obesity and/or anti-diabetic activities and including an amino acid sequence of SEQ ID NO: 1 or SEQ ID NO: 2, a pharmaceutical composition for prevention and/or treatment of obesity and/or diabetes, the pharmaceutical composition comprising, as an active ingredient, at least one selected from the group consisting of the peptides, and a use of the peptides.

BACKGROUND ART

Recently in Korea, the intake of lipid components from food has increased due to economic growth and westernized food lives, and metabolic diseases, such as obesity, diabetes, hyperlipidemia, hypertension, arteriosclerosis, and fatty liver, are increasing due to lack of exercise or the like. Obesity may hurt the appearance of slim body types that young people like, and persisting obesity may cause a variety of diseases.

Current medicines for treating obesity may be largely divided into medicines that act on the central nervous system to affect appetite and medicines that act on the gastrointestinal tract to inhibit absorption. The medicines acting on the central nervous system include, depending on the mechanism of each medicine, those inhibiting serotonin (5-HT) in the central nervous system, such as fenfluramine and dexfenfluramine, those acting on noradrenaline in the nervous system, such as ephedrine and caffeine, and those acting on both serotonin and noradrenaline in the central nervous systems to inhibit obesity, such as sibutramine. The foregoing medicines are available in the market.

In addition, a typical example of the medicines that act on the gastrointestinal tract to inhibit obesity is orlistat, which reduces lipid absorption by inhibiting lipase in the gastrointestinal tract and is approved as a medicine for obesity. However, among the existing medicines, fenfluramine and the like were recently withdrawn from the market due to the side effects thereof, such as pulmonary hypertension or heart valve disease, and other medicines are inapplicable to patients with renal diseases or heart failure due to the occurrence of reduced blood pressure, lactic acidosis, and the like.

Diabetes is a type of metabolic disease wherein impaired insulin secretion or absence of normal functions occurs (DeFronzo, 1988), and is characterized by hyperglycemia, for example, increased blood glucose levels. Hyperglycemia causes several symptoms and signs and results in the discharge of glucose into urine. In recent years, the incidence of diabetes is an explosively growing trend due to increased obesity rates, especially, increased abdominal obesity.

The number of diabetic patients was estimated to be 170 million worldwide in 2000 and is expected to reach 370 million in 2030, but according to a recent analysis report, the number of diabetic patients already reached about 350 million worldwide in 2008 (Danaei et al., 2011), which is far worse than expected. It is reported that about 80% or more of type 2 diabetic patients are obese while less than 10% of obese patients have diabetes (Harris et al. 1987). Such correlation between diabetes and obesity is due to the fact that adipokines and free fatty acids are irregularly secreted to induce fatty acids to accumulate in insulin-sensitive tissues, such as beta cells, kidneys, liver, and heart, resulting in lipotoxicity. If left without suitable treatment, chronic hyperglycemia is accompanied by various pathological symptoms in the body, and representative symptoms include retinopathy, renal dysfunction, neuropathy, and vascular disorder. Indispensable for preventing such complications is effective blood glucose management.

Nowadays, the control of blood glucose is accomplished by correction of lifestyle (diet therapy or exercise therapy), and medicinal therapy. However, diet therapy or exercise therapy is difficult to strictly manage and practice, with limitations of the effects thereof. Hence, most patients with diabetes rely on the control of blood glucose by medicines, such as insulin, insulin secretagogues, insulin sensitizers, and hypoglycemic agents, as well as correction of lifestyle.

The insulin that is produced using a recombinant method is used as a drug indispensable to type 1 diabetic patients, and type 2 diabetic patients failing to control blood glucose. Such insulin is advantageous in blood glucose control, but has disadvantages of aversion to syringe needles, difficulty in administration, hypoglycemic risk, and weight gain.

Meglitinides, which are a kind of insulin secretagogue, are fast-acting agents and are taken before meals, and examples thereof include NovoNorm (repaglinide), Fastic (nateglinide), and Glufast (mitiglinide). Insulin sensitizers are characterized by almost no hyperglycemic incurrence when taken alone, and may be exemplified by biguanide drugs, such as metformin, and thiazolidinedione drugs, such as Avanida (rosiglitazone) and Actos (pioglitazone).

Recently, GLP-1 agonists have been developed using the action of glucagon-like peptide-1, which is an insulin secretion-stimulating hormone, and include exenatide and Victoza (liraglutide). In addition, dipeptidyl peptidase-4 (DPP-4) inhibitors, which inhibit the action of DPP, an enzyme responsible for the rapid inactivation of GLP-1, are newly developed drugs and are representatively exemplified by Januvia (ingredient name: sitagliptin).

However, these medicines are reported to have side effects of hepatotoxicity, gastrointestinal disorders, cardiovascular disorders, and carcinogenicity, and such medicines cause high annual treatment costs, resulting in a barrier to the treatment of diabetes. Indeed, health care costs of pre-diabetes and diabetes approached about 200 trillion won in the USA as of 2007 (Dall et al., 2010), and health care costs of obesity are also near 150 trillion won only in the USA as of 2008 (Finkelstein et al., 2009). Therefore, there is an urgent need for the development of a drug that can effectively lower blood glucose levels and can be applied to both diabetes and obesity-induced diabetes, with few side effects.

Above all, the present inventors have recently paid attention to energy metabolism-regulating mechanisms in order to find an improved method for the treatment of obesity, and have made research of signals responsible for lipid accumulation and proteins affecting lipid accumulation upon the intake of high-fat diets in humans, with the premise that the compound to be developed should of higher safety (lower toxicity). Though the research on signals for suppressing the expression of proteins responsible for lipid accumulation and for breaking down accumulated lipid and on proteins involved in the signaling, the present inventors developed peptides that stimulate lipolysis. In addition, the peptides of the present invention show outstanding therapeutic efficacy on diabetes and obesity-induced diabetes. The lipid accumulation induced by high-fat diets, the suppression of insulin signaling attributed to lipid accumulation in the liver or muscle, and the resulting insulin tolerance are causes of diabetes.

DETAILED DESCRIPTION OF THE INVENTION

Technical Problem

The present inventors endeavored to develop a plurality of excellent peptides having biologically effective activity, and as a result, established that a peptide composed of an amino acid sequence of SEQ ID NO: 1 or SEQ ID NO: 2 suppresses lipid accumulation induced by a high-fat diet and breaks down the already accumulated lipid, thereby showing an anti-obesity effect as well as an excellent blood glucose lowering effect, and thus the present inventors completed the present invention.

Therefore, an aspect of the present invention is to provide a peptide composed of an amino acid sequence of SEQ ID NO: 1 or SEQ ID NO: 2 and having anti-obesity and/or anti-diabetic activities.

Another aspect of the present invention is to provide a pharmaceutical composition for preventing and/or treating an obesity, the pharmaceutical composition comprising at least one peptide selected from the group consisting of peptides consisting of the amino acid sequences of SEQ ID NO: 1 and SEQ ID NO: 2.

Still another aspect of the present invention is to provide a pharmaceutical composition for preventing and/or treating diabetes, the pharmaceutical composition comprising at least one peptide selected from the group consisting of peptides consisting of the amino acid sequences of SEQ ID NO: 1 and SEQ ID NO: 2.

Technical Solution

In accordance with an aspect of the present invention, there is provided a peptide having anti-obesity and/or anti-diabetic activities and consisting of the amino acid sequence of SEQ ID NO: 1 or SEQ ID NO: 2.

The present inventors endeavored to develop a plurality of excellent peptides having biologically effective activity, and as a result, established that a peptide composed of an amino acid sequence of SEQ ID NO: 1 or SEQ ID NO: 2 suppresses lipid accumulation induced by a high-fat diet and breaks down the already accumulated lipid, thereby showing an anti-obesity effect as well as an excellent blood glucose lowering effect.

The peptide of the present invention may include the amino acid sequence of SEQ ID NO: 1 or SEQ ID NO: 2, and for example, may be composed of the amino acid sequence of SEQ ID NO: 1 or SEQ ID NO: 2.

The peptides show an excellent anti-obesity effect by suppressing lipid accumulation, decreasing the size of adipocytes, and increasing the expressions of the lipolysis factors pHSL, AMPK-α1, and CGI-58 to break down already accumulated lipids.

As used herein, the term "obesity" refers to an excessive accumulation of body fat in the body.

The peptides reduce lipid accumulation in adipocytes and degrade the differentiation into adipocytes.

The peptides increase lipolysis. The lipolytic effect of the peptides of the present invention is attained by increasing the expressions of the lipolytic enzyme phospho-hormone-sensitive lipase (pHSL) and the lipolysis factor comparative gene identification-58 (CGI-58).

The peptides exhibit anti-obesity activity by regulating the expression of HSL gene to break down stored triglycerides into fatty acids and glycerols.

As shown in examples below, triglycerides stored in adipocytes are hydrolyzed into free fatty acids and glycerols, which are then released, when the adipocytes are treated with the peptides. These results indicate that the peptides of the present invention hydrolyze triglycerides, which are stored in adipocytes, into free fatty acids and glycerols to release the free fatty acids and glycerols out of the cells.

In addition, the treatment with the peptides reduced the content of triglycerides in adipocytes and increased the secretion of glycerols, which are triglyceride breakdown products, out of the adipocytes.

In addition, the gene expression of HSL, which breaks down triglycerides into free fatty acids and glycerols in adipose tissues, was increased by the treatment with the peptides.

Therefore, these results indicate that the peptides of the present invention show an anti-obesity effect by lipolysis through the expression increase of HSL gene in adipose tissues.

The peptide consisting of the amino acid sequence of SEQ ID NO: 1 or SEQ ID NO: 2 has an excellent anti-diabetic effect by effectively lowering blood glucose, increasing the expression of adiponectin and AMPK, which indicate the improvement in insulin resistance, increasing the expression of the glucose transporter GLUT4, and increasing the expression of IRS-1, which is an insulin receptor signaling protein.

As used herein, the term "diabetes" refers to a chronic disease characterized by a relative or absolute shortage in insulin, causing glucose-intolerance. The diabetes in the present invention is preferably type 2 diabetes. Type 2 diabetes is the insulin-independent diabetes, and is caused by an insufficient secretion of insulin after eating or by insulin resistance.

The peptides increase the expression of adiponectin in insulin resistance conditions. The adiponectin in the blood decreases in the presence of insulin resistance, and the adiponectin increases when the insulin resistance is improved by administration of a medicine increasing insulin sensitivity (Characteristics of blood adiponectin in newly diagnosed type 2 diabetic patients, 2007, Diabetes Vol 31, 6). That is, the peptides of the present invention, which increase adiponectin in insulin resistance conditions, shows an effect of improving insulin resistance, and thus show preventive or treatment efficacy for diabetes.

In addition, the peptides increase the expression of GLUT4 in insulin resistance conditions. GULT4 is an insulin transporter, and under the stimulation by insulin, GULT4 in the cell migrates into the plasma membrane to promote the transport of glucoses. Therefore, GULT4 lowers blood glucose by facilitating the inflow of blood glucose into cells. That is, the anti-diabetic effect increases as the activation and expression of GLUT4 involved in glucose transport increase.

In addition, the peptides increase the expression of IRS-1 in insulin resistance conditions. Insulin receptor substrate 1, 2 (IRS-1, 2) is an insulin substrate protein, and when p85 binds to the insulin receptor 1, 2, phosphatidylinositol 3 kinase (PI3K) is transmitted by an intermediate, such as Akt, and induces glucose transport.

In addition, the peptides increase the expression of AMPK-α1 in insulin resistance conditions.

AMPK is an enzyme that acts as a sensor for energy homeostasis in cells, and when the intracellular energy is reduced by metabolic stress or exercise, AMPK is activated to suppress an ATP consumption procedure (for example, fatty acid synthesis and cholesterol synthesis) and stimulate an ATP production procedure (for example, fatty acid oxidation and glycolysis (Hardie DG: AMP-activated/SNF1 protein kinases: conserved guardians of cellular energy. Nat Rev Mol Cell Biol 8:774-785, 2007).

The effect of AMPK activation is involved in target organs (liver, muscle, fat, pancreas) closely related to energy metabolism regulation (Zhang B B, Zhou G, Li C: AMPK: an emerging drug target for diabetes and the metabolic syndrome. Cell Metab 9:407-416, 2009).

The activation of AMPK suppresses the synthesis of fatty acids and cholesterols and stimulates the oxidation of fatty acids in the liver. The activation of AMPK stimulates the oxidation of fatty acids and the absorption of glucoses in skeletal muscles and suppresses lipolysis and lipogenesis in adipocytes. In addition, the increases of AMPK activation and expression induce glucose lowering through the suppression of glucogenesis in the liver (Foretz M, et al., *Diabetes* 54:1331-1339, 2005, Lochhead P A, et al., *Diabetes* 49:896-903, 2000).

As used herein, the term "peptide" refers to a linear molecule formed by amino acid residues linked to each other via peptide linkages.

The peptides of the present invention may be prepared by chemical synthesis methods known in the art, especially, solid-phase synthesis techniques (Merrifield, *J. Amer. Chem. Soc.* 85:2149-54(1963); Stewart, et al., *Solid Phase Peptide Synthesis,* 2nd. ed., Pierce Chem. Co.: Rockford, 111(1984)) or liquid-phase synthesis techniques (U.S. Pat. No. 5,516, 891).

The peptides of the present invention may have a modification induced at the N-terminal or C-terminal thereof in order to select a part of an amino acid sequence and increase the activity thereof.

For example, the C-terminal modification may be a modification of the C-terminal of the peptide into a hydroxy group (—OH), an amino group (—NH$_2$), an azide group (—NHNH$_2$), or the like, but is not limited thereto.

In addition, the N-terminal modification may be an attachment of at least one protecting group selected from the group consisting of an acetyl group, a fluorenyl methoxy carbonyl group, a formyl group, a palmitoyl group, a myristyl group, a stearyl group, and polyethylene glycol (PEG) to the N-terminal of the peptide, but is not limited thereto. The protecting group protects the peptide of the present invention from in vivo protein cleavage enzymes.

The N-terminal and/or C-terminal modification of the peptides improves the stability of the peptides, and this modification allows the peptides of the present invention to have an increased half-life at the time of in vivo administration, thereby having a high half-life.

The foregoing amino acid modification functions to significantly improve the stability of the peptides of the present invention. As used herein, the term "stability" refers to storage stability (e.g., room-temperature stability) as well as in vivo stability. The foregoing protective group acts to protect the peptides of the present invention from the attack by protein cleavage enzymes in vivo.

In accordance with another aspect of the present invention, there is provided a pharmaceutical composition for preventing and/or treating an obesity, the pharmaceutical composition comprising, as an active ingredient, at least one peptide selected from the group consisting of peptides consisting of the amino acid sequences of SEQ ID NO: 1 and SEQ ID NO: 2.

The peptides have excellent functions of inhibiting lipogenesis and breaking down lipids, and thus can be used in the prevention and/or treatment of obesity.

The pharmaceutical composition may be a pharmaceutical composition comprising (a) a pharmaceutically effective amount of the peptide or a composite of the peptide; and/or (b) a pharmaceutically acceptable carrier.

As used herein, the term "pharmaceutically effective amount" refers to an amount sufficient to attain the efficacy or activity of the foregoing peptide.

The pharmaceutically acceptable carrier contained in the pharmaceutical composition is normally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methyl hydroxybenzoate, propyl hydroxybenzoate, talc, magnesium stearate, and/or mineral oil.

The pharmaceutical composition of the present invention may further contain a lubricant, a wetting agent, a sweetening agent, a flavoring agent, an emulsifier, a suspending agent, a preservative, and the like, in addition to the above ingredients.

Suitable pharmaceutically acceptable carriers and agents are described in detail in *Remington's Pharmaceutical Sciences* (19th ed., 1995).

The pharmaceutical composition of the present invention may be administered orally or parenterally, and preferably parenterally. Examples of the parenteral administration may include intramuscular injection, intravenous injection, subcutaneous injection, intraperitoneal injection, topical administration, and transdermal administration.

A proper dose of the pharmaceutical composition of the present invention may vary depending on various factors, such as the method for formulation, the manner of administration, patient's age, body weight, gender, morbidity, and diet, the time of administration, the excretion rate, and the response sensitivity. Meanwhile, the preferable dose of the pharmaceutical composition of the present invention is 0.0001-1000 μg per day.

The pharmaceutical composition of the present invention may be formulated into a unit dosage form or a multi-dose container using a pharmaceutically acceptable carrier and/or excipient according to the method easily conducted by a person having ordinary skills in the art to which the present invention pertains.

Here, the dosage form may be a solution in an oily or aqueous medium, a suspension, and/or an emulsion, an extract, a powder, granules, a tablet, and/or a capsule, and may further contain a dispersant and/or a stabilizer, but is not limited thereto.

In accordance with still another aspect of the present invention, there is provided a pharmaceutical composition for preventing and/or treating of diabetes, the pharmaceutical composition comprising, as an active ingredient, at least one peptide selected from the group consisting of peptides consisting of the amino acid sequences of SEQ ID NO: 1 and SEQ ID NO: 2.

The peptides of the present invention effectively lower the increased blood glucose and show insulin resistance improvement efficacy, and thus can be used in the prevention or treatment of diabetes.

Advantageous Effects

The present invention relates to a peptide having anti-obesity and/or anti-diabetic activities and consisting of the amino acid sequence of SEQ ID NO: 1 or SEQ ID NO: 2, and to a pharmaceutical composition, comprising, as an active ingredient, at least one selected from the group consisting of the peptides, for preventing and/or treating an obesity and/or diabetes. The peptides has not only an excellent anti-obesity effect by suppressing lipid accumulation, decreasing the size of adipocytes, and increasing the expressions of the lipolysis factors pHSL, AMPK-α1, and CGI-58 to break down already accumulated lipids, but also an excellent effect on diabetes by effectively by effectively lowering blood glucose, increasing the expressions of adiponectin and AMPK, which indicate the improvement in insulin resistance, increasing the glucose transporter GLUT4, and increasing the expressions of IRS-1, which is an insulin receptor signaling protein. Accordingly, the peptides can be favorably used in the prevention or treatment of obesity and/or diabetes.

BRIEF DESCRIPTION OF THE DRAWINGS

FIG. 1b is a graph confirming, through oil red O staining, accumulated lipid when cells were treated with a peptide composed of the amino acid sequence of SEQ ID NO: 1 according to an embodiment of the present invention.

FIG. 1c shows photos confirming, through oil red O staining, accumulated lipids when cells were treated with a peptide composed of the amino acid sequence of SEQ ID NO: 2 according to an embodiment of the present invention.

FIG. 1d is a graph confirming, through oil red O staining, accumulated lipids when cells were treated with a peptide composed of the amino acid sequence of SEQ ID NO: 2 according to an embodiment of the present invention.

FIG. 2a is a graph showing the measurement results of the amount of glycerol secretion when cells were treated with a peptide composed of the amino acid sequence of SEQ ID NO: 1 according to an embodiment of the present invention.

FIG. 2b is a graph showing the measurement results of the amount of glycerol secretion when cells were treated with a peptide composed of the amino acid sequence of SEQ ID NO: 2 according to an embodiment of the present invention.

FIG. 4a shows photos showing the measurement results of the number of adipocytes and the area thereof after the mouse adipose tissues were treated with a peptide composed of the amino acid sequence of SEQ ID NO: 1 according to an embodiment of the present invention.

FIG. 5b shows photos showing the measurement results of the expression level of phospho-HSL protein, which is an important protein in lipid synthesis, when cells were treated with a peptide composed of the amino acid sequence of SEQ ID NO: 2 according to an embodiment of the present invention.

FIG. 6b is a graph showing the measurement results of the change in blood glucose when blood was taken after mice were supplied with a high-fat diet and a peptide composed of the amino acid sequence of SEQ ID NO: 2 according to an embodiment of the present invention.

FIG. 7a shows the expression changes of adiponectin and GLUT5 after insulin resistance-induced cells were treated with a peptide composed of the amino acid sequence of SEQ ID NO: 1 according to an embodiment of the present invention.

FIG. 8a shows the measurement results of the expression changes of IRS-1 and AMPK-α1 after insulin resistance-induced cells were treated with a peptide composed of the amino acid sequence of SEQ ID NO: 1 according to an embodiment of the present invention.

FIG. 8b shows the measurement results of the expression changes of IRS-1 and AMPK-α1 after insulin resistance-induced cells were treated with a peptide composed of the amino acid sequence of SEQ ID NO: 2 according to an embodiment of the present invention.

BEST MODE FOR CARRYING OUT THE INVENTION

Figure 1A:
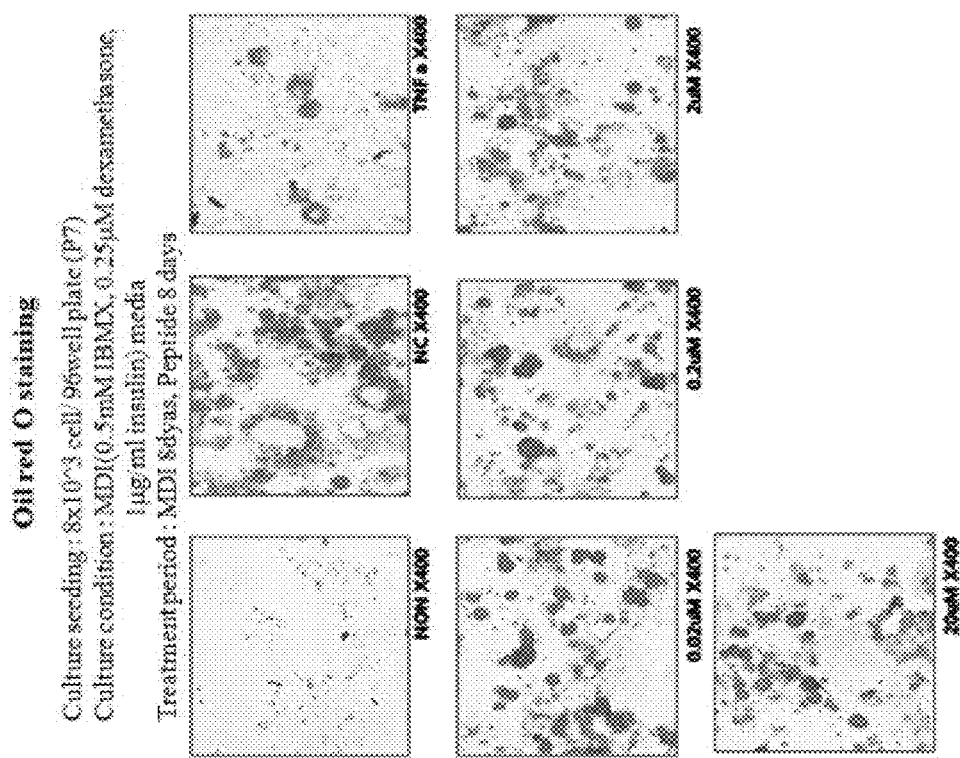
FIG. 1a shows photos confirming, through oil red O staining, accumulated lipids when cells were treated with a peptide composed of the amino acid sequence of SEQ ID NO: 1 according to an embodiment of the present invention.

The present invention relates to a peptide having anti-obesity activity or anti-diabetic activity and including an amino acid sequence of SEQ ID NO: 1 or SEQ ID NO: 2.

MODE FOR CARRYING OUT THE INVENTION

Hereinafter, the present invention will be described in detail with reference to examples. These examples are only for illustrating the present invention more specifically, and it will be apparent to those skilled in the art that the scope of the present invention is not limited by these examples.

EXAMPLES

Synthesis Example 1: Peptide Synthesis 700 mg of chlorotrityl chloride resin (CTL resin, Nova Biochem Cat No. 01-64-0021) was placed in a reaction container, and 10 ml of methylene chloride (MC) was added, followed by stirring for 3 minutes.

After the solution was removed, 10 ml of dimethyl formamide (DMF) was added, followed by stirring for 3 minutes, and then the solvent was again removed. After 10 ml of a dichloromethane solution was placed in the reactor, and 200 mmole Fmoc-Ser(tBu)-OH (Bachem, Swiss) and 400 mmole diisopropyl ethylamine (DIEA) were added thereto, the mixture was well dissolved with stirring, followed by reaction with stirring for 1 hour.

After the reaction, washing was conducted, and then methanol and DIEA (2:1) were dissolved in dichloromethane (DCM) to conduct reaction for 10 minutes, followed by washing with excessive DCM/DMF (1:1).

After the solution was removed, 10 ml of dimethyl formamide (DMF) was added, followed by stirring for 3 minutes, and then the solvent was again removed. 10 ml of a deprotection solution (20% piperidine/DMF) was placed in the reaction container, followed by stirring at room temperature for 10 minutes, and then the solution was removed.

An equal amount of a deprotection solution was added, and then the reaction was again maintained for 10 minutes, and thereafter, the solution was removed, followed by washing twice with DMF, once with MC, and once with DMF, for 3 minutes each, thereby preparing Ser (tBu)-CTL Resin.

10 ml of a DMF solution was placed in a new reactor, and 200 mmol Fmoc-Lys(Boc)-OH (Bachem, Swiss), 200 mmol HoBt, and 200 mmole Bop were added, and the mixture was well dissolved with stirring.

After 400 mmole DIEA was added to the reactor in two divided portions, stirring was conducted for at least 5 minutes until all solids were dissolved. The dissolved amino acid mixed solution was added to the reaction container containing the deprotected resin therein, and the reaction was conducted with stirring at room temperature for 1 hour.

After the reaction liquid was removed, stirring was conducted using a DMF solution three times for 5 minutes each, followed by removal. A small amount of the reaction resin was taken to check the extent of reaction using the Kaiser test (Ninhydrin test).

The deprotection reaction was twice conducted using a deprotection solution in the same manner as described above, thereby preparing Lys(Boc)-Ser(tBu)-CTL Resin. After sufficient washing with DMF and MC, the Kaiser test was again conducted, and then the following amino acid attachment test was conducted in the same manner as described above.

A chain reaction was conducted in the order of Fmoc-Arg(Pbf)-OH, Fmoc-Glu(OtBu)-OH, and Fmoc-Lys(Boc)-OH according to the selected amino acid sequence. The Fmoc-protecting group was removed by reaction twice with the deprotection solution for 10 minutes for each and then well washed. After acetic anhydride, DIEA, and HoBt were added to conduct acetylation for 1 hour, the prepared peptidyl resin was washed with DMF, MC, and methanol three times each, dried under the slow flow of nitrogen gas, and completely dried by vacuum decompression under P2O5. Thereafter, 30 ml of a leaving solution [95% trifluoroacetic acid (TFA), 2.5% distilled water, and 2.5% thioanisole] was added, and the reaction was maintained for 2 hours while the mixture was intermittently stirred at room temperature.

The resin was obtained through filtration, washed with a small amount of a TFA solution, and then mixed with the stock solution.

After distillation was conducted under reduced pressure to reduce the total volume by half, 50 ml of cold ether was added to induce precipitation, and then the precipitates were collected by centrifugation, followed by washing twice with cold ether.

The stock solution was removed, followed by sufficient drying under nitrogen, thereby synthesizing 0.77 g of Lys-Glu-Arg-Lys-Ser peptide 1 before purification (yield: 89.2%).

The molecular weight thereof was determined as 646.7 (theoretical value: 646.7) by using a molecular weight analysis system.

Another peptide of SEQ ID NO: 2 was also synthesized by the method as described above.

TABLE 1

| SEQ ID NO | Amino acid sequence | Analysis value (Mass spectrometer) | |
|---|---|---|---|
| | | Analytic value | Theoretical value |
| 1 | Lys-Glu-Arg-Lys-Ser | 646.7 | 646.7 |
| 2 | His-Glu-Thr-Phe-Glu | 661.6 | 661.7 |

Example 1: Oil Red O Staining

In order to measure the lipid accumulation inhibitory effect by the peptides of the present invention, 3T3-L1 cells were seeded in 24-well plate at $2 \times 10^4$ cells/well, followed by culture, and then the medium was exchanged with a differentiation medium containing 10 ug/ml insulin, 0.1 uM dexamethasone, and 0.5 uM IBMX, followed by treatment with the peptides having different concentrations.

Thereafter, the medium was exchanged into a medium containing 10 ug/ml insulin every two days, and on day 9 of differentiation induction, an oil-red-red O staining assay was conducted.

The cells were washed with PBS, immobilized by the treatment with 4% para-form aldehyde for 10 minutes, washed with distilled water, and then cultured in 60% isopropanol for 5-10 minutes. The immobilized cells were stained with an oil red solution [1% Oil Red in isopropanol was diluted in dH$_2$O in ratio of 6:4 (vol/vol)] for 30 minutes, and then again washed with PBS. The stained cells were observed by an optical microscope, followed by washing with distilled water, and 1 ml of 100% isopropanol was added thereto, followed by stirring at 4° C. The next day, quantification was conducted at 510 nm.

As can be seen from FIGS. 1a to 1d, it could be confirmed through oil red O staining that the degree of lipid accumulation in the cells was reduced when the cells were treated with the peptides of SEQ ID NO: 1 and SEQ ID NO: 2.

Example 2: Glycerol Assay (Lipolysis Induction)

Adipocytes store extra energy in the form of triglycerides in lipid droplets, and when energy is needed, the triglycerides are broken down into fatty acids and glycerols by enzymes, such as adipose triglyceride lipase, HSL, and monoglyceride lipase, to produce energy, or the triglycerides are used in cell signaling or lipid synthesis. The measurement of free glycerol release is for evaluating the lytic effect of the glycerides accumulated in fact cells.

In order to measure the lipolytic effect by the peptides of the present invention, the mouse adipose tissue was taken and cultured in 100-mm dish (DMEM) for one day. Thereafter, the adipose tissue was cut into equal weight, transferred onto 24-well plate, treated with the peptides, and cultured for 48-72 hours. Each 100 ul of the medium was collected according to the treatment period, and subjected to glycerol assay. The results are shown in FIGS. 2a and 2b.

As can be confirmed from FIG. 2a, the secretion of glycerol in the tissue was increased by the treatment with the peptide including the amino acid sequence of SEQ ID NO: 1.

As can also be confirmed from FIG. 2b, the secretion of glycerol was increased by the treatment with the peptide including the amino acid sequence of SEQ ID NO: 2 dependently on the concentration of the peptide, compared with a control group NC. The secretion of glycerol was increased by 22% by high-concentration peptide treatment.

Example 3: CGI-58 RT-PCR

Total RNA was extracted using Qiagen RNeasy kit. For synthesis of single-stranded DNA from RNA, 3 mg of RNA, 2 mg of random hexamer, and DEPC-treated water were added, followed by reaction for 5 minutes at 65° C. 5× first strand buffer, 0.1 M DTT, 10 mM of dNTP, and reverse transcriptase were added to reach a total volume of 20 ml, followed by reaction at 42° C. for 1 hour. After heating at 95° C. for 5 minutes again, 10 ml of distilled water was added to make a final volume, 40 ml, of cDNA.

PCR was conducted by mixing 3 ml of cDNA, 10 pmole of CGI 58 gene-specific primer, 10× Tag buffer, 10 mM dNTP, and i-Tag DNA synthetase. PCR conditions were: 94° C. for 30 seconds, 55-56° C. for 30 seconds, and 72° C. for 30 seconds. Cycle number genes were analyzed in the conditions in which the PCR results could be exponentially amplified. 5 ml of PCR product was obtained, electrophoresed on 1% agarose gel, and stained with ethidium bromide. The results are shown in FIGS. 3a to 3c.

TABLE 2

| SEQ ID NO | Primer | Sequence (5'-3') |
|---|---|---|
| 3 | CGI 58_F | TGTGCAGGACTCTTACTTGGCAGT |
| 4 | CGI 58_R | GTTTCTTTGGGCAGACCGGTTTCT |

Figure 3A:
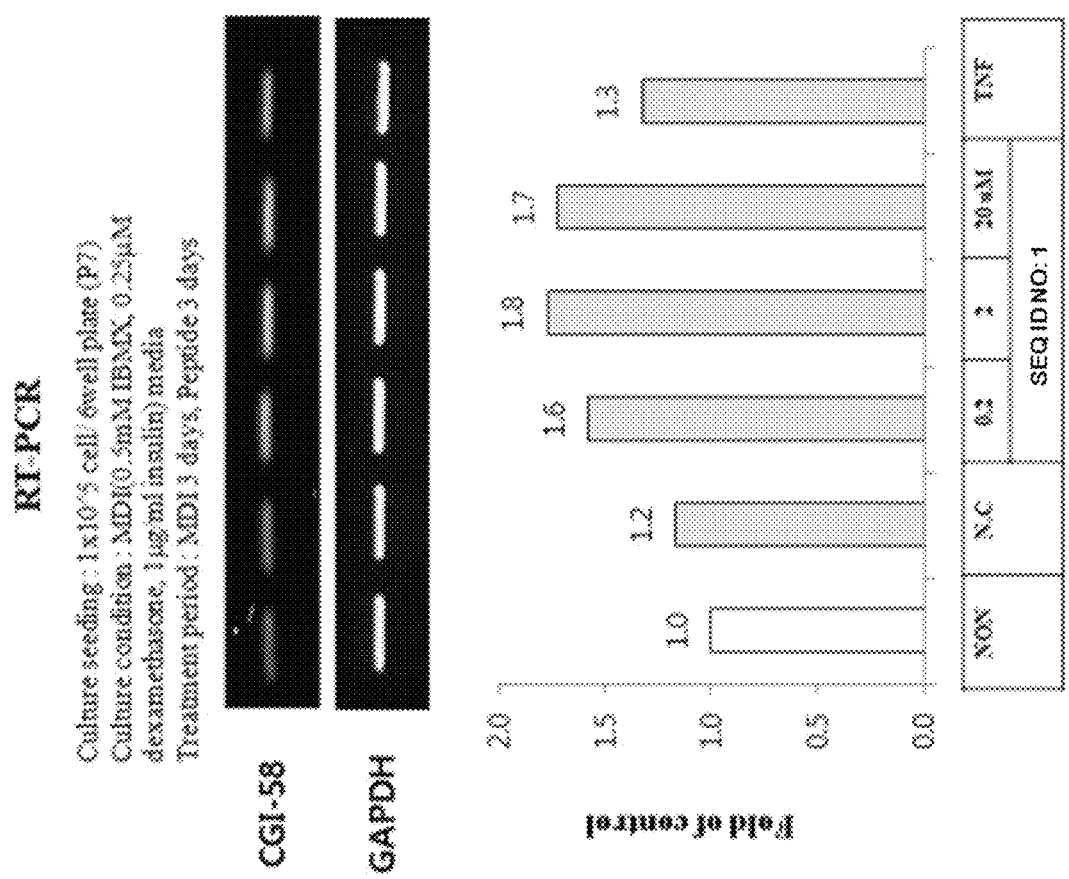
FIG. 3a shows the measurement results of the expression level of CGI-58, which is a gene involved in the procedure of breaking down accumulated lipids, when cells were treated with a peptide composed of the amino acid sequence of SEQ ID NO: 1 according to an embodiment of the present invention.
Figure 3B:
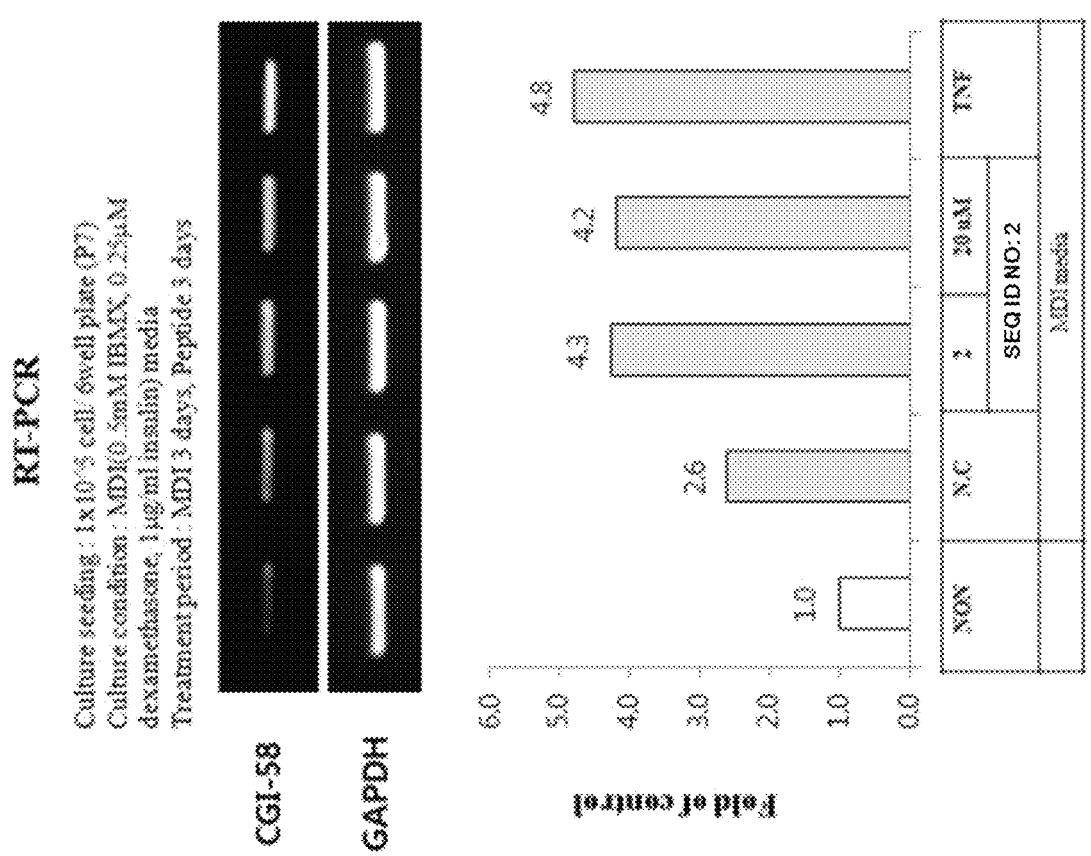
FIG. 3b shows the measurement results of expression level of CGI-58, which is a gene involved in the procedure of breaking down accumulated lipids, when cells were treated with a peptide composed of the amino acid sequence of SEQ ID NO: 2 according to an embodiment of the present invention.

As can be confirmed from FIGS. 3a to 3c, as a result of confirming the degree of intracellular CGI 58 expression through RT-PCR, the expression of the lipolysis factor CGI-58 was increased by the treatment with the peptide including the amino acid sequence of SEQ ID NO: 1 or SEQ ID NO: 2.

Example 4: Histological Analysis (Lipolysis Induction)

The mouse adipose tissue was taken and cultured in 100-mm dish (DMEM) for one day. Thereafter, the adipose tissue was cut into equal weight, transferred onto 24-well plate, treated with the peptides, and cultured for 48-72 hours. Each tissue slice was subjected to H&E staining. The photo files obtained from microscopic photographing were divided into compartments through Image J, and analyzed using a program that can compare the sizes of each compartment. Through this, the area of the total number of cells can be obtained, and the average area obtained by dividing the area by the total number of cells can also be obtained. The results may be expressed differently depending on the degree of staining. However, correction can be made by adjusting the threshold value in the beginning, and the results were obtained after the cells with relatively small areas from the comparison with the original file were removed.

Figure 4B:
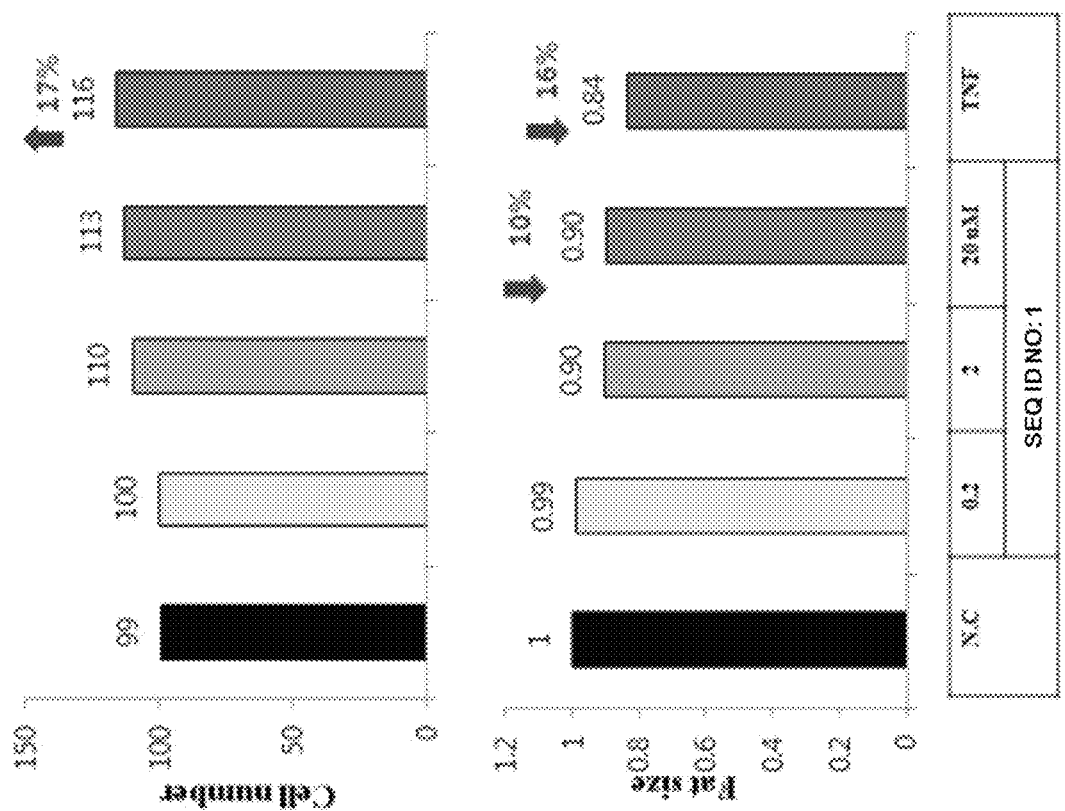
FIG. 4b shows graphs showing the measurement results of the number of adipocytes and the area thereof after the mouse adipose tissues were treated with a peptide composed of the amino acid sequence of SEQ ID NO: 1 according to an embodiment of the present invention.

As can be confirmed from FIGS. 4a and 4b, the number of adipocytes was increased and the lipid area was reduced as the concentration of the peptide of SEQ ID NO: 1 increased.

An increase in the number of adipocytes per unit area may indicate that the size of adipocytes, that is, the lipid accumulation in the adipocytes was decreased.

Example 5: Immunohistochemical Staining (Lipolysis Induction)

In order to investigate a mechanism by which the peptides of the present invention stimulate the lysis of triglycerides to suppress the lipid accumulation in adipocytes, the effect of the peptides of the present invention on HSL gene expression was examined. HSL enzyme is known as a lipolytic enzyme that breaks down triglycerides into free fatty acids and glycerols when the HSL enzyme breaks down lipids in the adipose tissue.

The mouse adipose tissue was taken and cultured in 100-mm dish (DMEM) for one day. Thereafter, the adipose tissue was cut into equal weight, transferred onto 24-well plate, treated with the peptides, and cultured for 48-72 hours. Each tissue slice was subjected to immunohistochemical staining using anti-pHSL antibody, and photographed by a fluorescent microscope. The results are shown in FIGS. 5a and 5b.

Figure 5A:
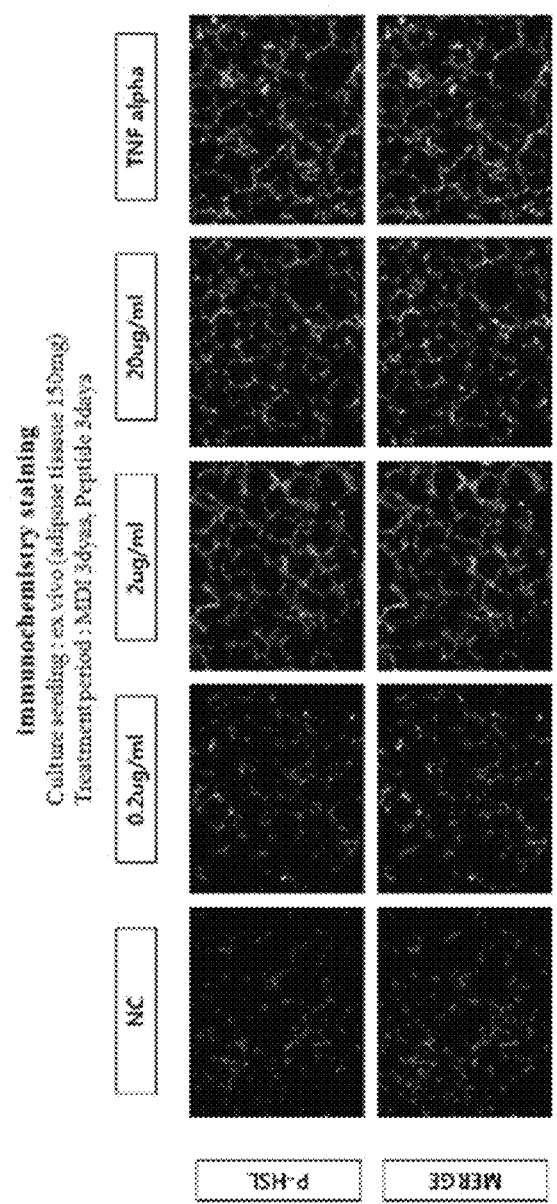
FIG. 5a shows photos showing the measurement results of the expression level of phospho-HSL protein, which is an important protein in lipid synthesis, when cells were treated with a peptide composed of the amino acid sequence of SEQ ID NO: 1 according to an embodiment of the present invention.

As can be confirmed from FIGS. 5a and 5b, the expression of hormone sensitive lipase (pHSL), which is a lipolytic factor, was increased by the peptide including the amino acid sequence of SEQ ID NO: 1 or SEQ ID NO: 2.

Example 6: Anti-Diabetic Efficacy Evaluation (In Vivo)

6-week-old C57BL/6J mice as experimental animals were purchased from Central Lab. Animal Inc. (Seoul, Korea), and then were used for experiments after acclimatization with a normal diet for 1 week. A high-fat feed was used from Research Diets, inc. (#product D12492).

The experimental animals were divided into a total of four groups, and three mice for each group were raised for 12 weeks. As shown in Table 3, experimental groups are a normal group (non group) fed with a normal diet, a group fed with a high-fat diet (NC group), a group fed with a high-fat diet and a peptide including the amino acid sequence of SEQ ID NO: 1 (oral administration), and a group fed with a high-fat diet and Januvia tablet (oral administration).

TABLE 3

| Obese mice (male) | | |
|---|---|---|
| Experimental groups | Dose | Number of animals |
| Non (normal diet group) | — | 3 |
| NC (60% fat diet group) | Oral (300 ul) | 3 |
| Peptide of SEQ ID NO: 1 (2 mg/ml) (60% fat diet group) | Oral (300 ul) | 3 |
| Januvia tablet (60% fat diet group) | Oral (300 ul) | 3 |
| Total number of animals | | 12 |

In addition, the experimental animals were divided into a total of five groups, and three mice for each group were raised for 12 weeks. As shown in Table 4, experimental groups are a normal group (non group) fed with a normal diet, a group fed with a high-fat diet (NC groups), a group fed with a high-fat diet and a peptide including the amino acid sequence of SEQ ID NO: 2 (oral administration), a group fed with a high-fat diet and a peptide including the amino acid sequence of SEQ ID NO: 2 (intraperitoneal administration), and a group fed with a high-fat diet and Januvia tablet (oral administration).

TABLE 4

Obese mice (male)

| Experimental groups | Experimental groups | Number of animals |
|---|---|---|
| Non (Normal diet group) | — | 3 |
| NC (60% fat diet group) | Oral (300 ul) | 3 |
| Peptide of SEQ ID NO: 2 (2 mg/ml) (60% fat diet group) | Oral (300 ul) | 3 |
| Peptide of SEQ ID NO: 2 (2 mg/ml) (60% fat diet group) | Intraperitoneal (300 ul) | 3 |
| Januvia tablet (60% fat diet group) | Oral (300 ul) | 3 |
| Total number of animals | | 12 |

Figure 6A:
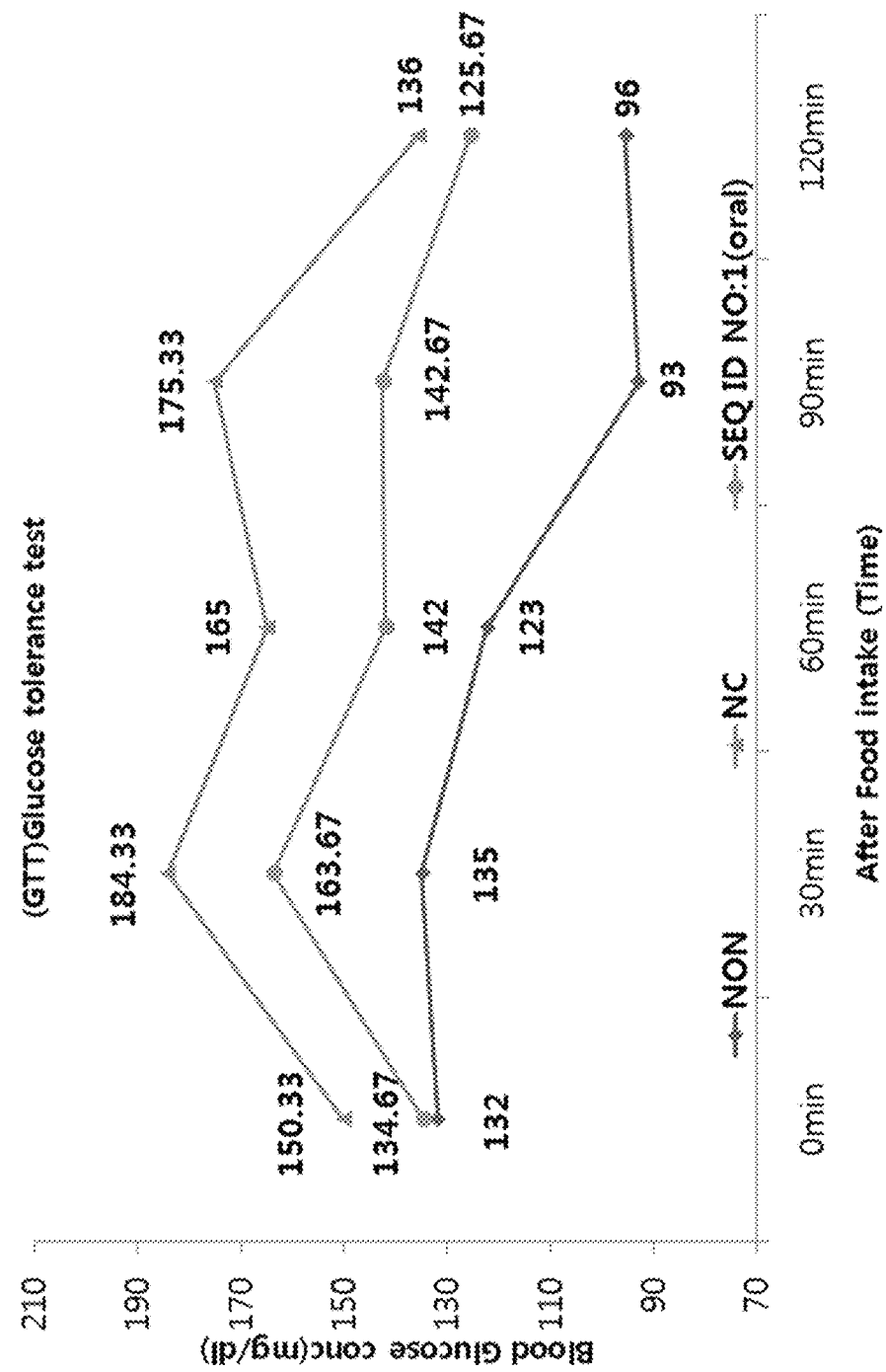
FIG. 6a is a graph showing the measurement results of the change in blood glucose when blood was taken after mice were supplied with a high-fat diet and a peptide composed of the amino acid sequence of SEQ ID NO: 1 according to an embodiment of the present invention.

After the pre-treatment with a peptide for 30 minutes, glucose (60 mg/300 ul distilled water) were orally administered, and then the blood glucose lowering effect over time was examined. The results are shown in FIGS. 6a to 6b and tables 5 and 6.

TABLE 5

|  | 0 min | 30 min | 60 min | 90 min | 120 min |
|---|---|---|---|---|---|
| NON | 123.00 | 128.00 | 119.00 | 87.00 | 94.00 |
|  | 141.00 | 142.00 | 126.00 | 99.00 | 97.00 |
| Mean | 132.00 | 135.00 | 123.00 | 93.00 | 96.00 |
| NC | 177.00 | 187.00 | 178.00 | 158.00 | 140.00 |
|  | 136.00 | 163.00 | 159.00 | 146.00 | 133.00 |
| Mean | 150.33 | 184.33 | 165.00 | 175.33 | 136.00 |
| SEQ ID NO: 1 (oral) | 145.00 | 203.00 | 162.00 | 170.00 | 130.00 |
|  | 165.00 | 190.00 | 195.00 | 158.00 | 115.00 |
| Mean | 134.67 | 163.67 | 142.00 | 142.67 | 125.67 |

TABLE 6

|  | 0 min | 10 min | 40 min | 80 min | 140 min | 200 min |
|---|---|---|---|---|---|---|
| NON | 126.00 | 123.00 | 128.00 | 119.00 | 87.00 | 94.00 |
|  | 150.00 | 141.00 | 142.00 | 126.00 | 99.00 | 97.00 |
| Mean | 138.00 | 132.00 | 135.00 | 123.00 | 93.00 | 96.00 |
| NC | 177.00 | 187.00 | 178.00 | 158.00 | 140.00 | 145.00 |
|  | 136.00 | 163.00 | 159.00 | 146.00 | 133.00 | 148.00 |
| Mean | 157.00 | 175.00 | 169.00 | 152.00 | 137.00 | 147.00 |
| SEQ ID NO: 2 (IP) | 145.00 | 203.00 | 162.00 | 170.00 | 130.00 | 129.00 |
|  | 165.00 | 190.00 | 195.00 | 158.00 | 115.00 | 94.00 |
| Mean | 155.00 | 197.00 | 179.00 | 164.00 | 123.00 | 112.00 |
| SEQ ID NO: 2 (oral) | 159.00 | 188.00 | 164.00 | 163.00 | 122.00 | 118.00 |
|  | 165.00 | 193.00 | 157.00 | 147.00 | 135.00 | 126.00 |
| Mean | 162 | 191 | 161 | 155 | 129 | 122 |

As can be confirmed from FIGS. 6a and 6b, the blood glucose increase by glucose was reduced in the group treated with the peptide including the amino acid sequence of SEQ ID NO: 1 or SEQ ID NO: 2 compared with the NC group.

Example 7: Anti-Diabetic Efficacy Evaluation (Adiponectin & GLUT4 RT-PCR)

Figure 7B:
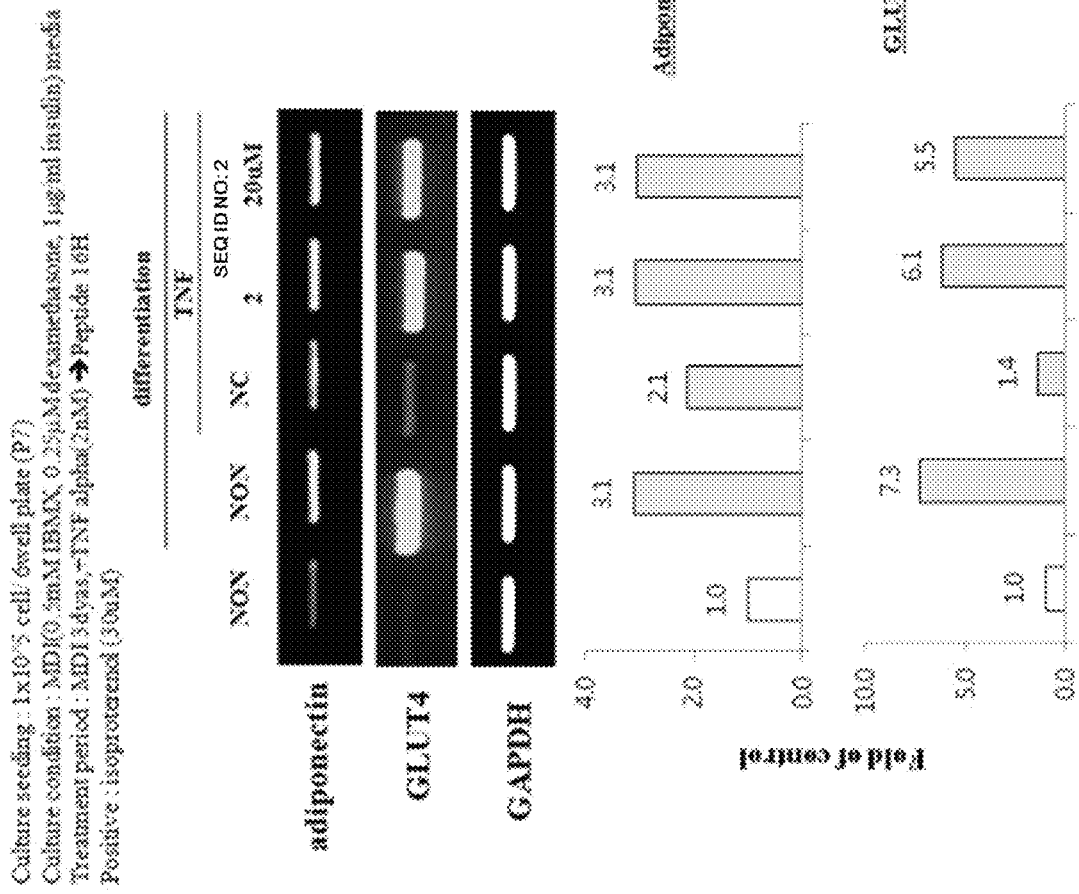
FIG. 7b shows the expression changes of adiponectin and GLUT5 after insulin resistance-induced cells were treated with a peptide composed of the amino acid sequence of SEQ ID NO: 2 according to an embodiment of the present invention.

After the insulin resistance conditions were configured by TNF-α treatment, the peptide treatment was conducted for 16 hours, followed by collection and then the resultant product was collected and the changes of respective factors were examined by RT-PCR. The results are shown in FIGS. 7a and 7b. RT-PCR conditions are the same as in example 3.

TABLE 7

| SEQ ID NO | Primer | Sequence (5'-3') |
|---|---|---|
| 5 | Adiponectin_F | GCCAATCTTCATCCAGTTGC |
| 6 | Adiponectin_R | CATCGTGAAGAAGGCATAGG |
| 7 | GLUT4_F | AAGATGGCCACGGAGAGAG |
| 8 | GLUT4_R | GTGGGTTGTGGCAGTGAGTC |

As can be seen from FIGS. 7a and 7b, the expression of adiponectin, which has been reduced by TNF-α treatment, was again increased by the treatment with the peptide including the amino acid sequence of SEQ ID NO: 1 or SEQ ID NO: 2. In addition, the expression of the glucose transporter GLUT4, which has been reduced by TNF-α treatment, was again increased by the treatment with the peptide.

Example 8: Anti-Diabetic Efficacy Evaluation (IRS-1 & AMPK-α1 RT-PCR)

After the insulin resistance conditions were configured by TNF-α treatment, the peptide treatment was conducted for 16 hours, followed by collection and then the resultant product was collected and the changes of respective factors were examined by RT-PCR. The results are shown in FIGS. 8a and 8b. RT-PCR conditions are the same as in example 3.

TABLE 8

| SEQ ID NO | Primer | Sequence (5'-3') |
|---|---|---|
| 9 | IRS-1_F | GCCAATCTTCATCCAGTTGC |
| 10 | IRS-1_R | CATCGTGAAGAAGGCATAGG |
| 11 | AMPK-α1_F | TGACCGGACATAAAGTGGCTGTGA |
| 12 | AMPK-α1_R | TGATGATGTGAGGGTGCCTGAACA |

As can be seen from FIGS. 8a and 8b, the expressions of AMPK-α1 and the insulin receptor signaling protein IRS-1, which have been reduced by TNF-α treatment, were again increased by the treatment with the peptide including the amino acid sequence of SEQ ID NO: 1. In addition, the expression of AMPK-α1, which has been reduced by TNF-α treatment, was again increased by the treatment with the peptide including the amino acid sequence of SEQ ID NO: 2.

INDUSTRIAL APPLICABILITY

The present invention relates to a peptide having anti-obesity and/or anti-diabetic activities and including an amino acid sequence of SEQ ID NO: 1 or SEQ ID NO: 2, a pharmaceutical composition for prevention and/or treatment of obesity and/or diabetes, the pharmaceutical composition containing, as an active ingredient, at least one selected from the group consisting of the peptides, and a use of the peptides.

The invention claimed is:

1. A peptide having anti-obesity activity or anti-diabetic activity, the peptide consisting of the amino acid sequence of SEQ ID NO: 1 or SEQ ID NO: 2, wherein the C-terminal end of the peptide is optionally modified by the presence of an amino group, or an azide group, and the N-terminal end of the peptide is optionally modified by the presence of a protecting group.

2. The peptide of claim 1, wherein the peptide reduces lipid accumulation in adipocytes.

3. The peptide of claim 1, wherein the peptide increases lipolysis.

4. The peptide of claim 1, wherein the peptide increases the expression of phospho-hormone-sensitive lipase (pHSL) or comparative gene identification-58 (CGI-58).

5. The peptide of claim 1, wherein the peptide decreases the size of adipocytes.

6. The peptide of claim 1, wherein the peptide lowers blood glucose.

7. The peptide of claim 1, wherein the peptide increases the expression of adiponectin, glucose transporter type 4 (GLUT4), insulin receptor substrate 1 (IRS-1), or AMP-activated protein kinase (AMPK)-α1.

8. The peptide of claim 1, wherein the C-terminal end of the peptide is modified by the presence of an amino group, or an azide group, or the N-terminal end of the peptide is modified by the presence of a protecting group.

9. The peptide of claim 8, wherein the N-terminal end of the peptide is modified by the presence of a protecting group, which is selected from the group consisting of an acetyl group, a fluorenyl methoxy carbonyl group, a formyl group, a palmitoyl group, a myristyl group, a stearyl group, and polyethylene glycol (PEG).

10. A method for treating obesity comprising:
administering a pharmaceutical composition comprising at least one peptide selected from a peptide consisting of the amino acid sequence of SEQ ID NO: 1 and a peptide consisting of the amino acid sequence of SEQ ID NO: 2, as an active ingredient, wherein the C-terminal end of either peptide is optionally modified by the presence of an amino group, or an azide group, and the N-terminal end of either peptide is optionally modified by the presence of a protecting group.

11. The method of claim 10, wherein the C-terminal end of either peptide is modified by the presence of an amino group, or an azide group, or the N-terminal end of either peptide is modified by the presence of a protecting group.

12. The method of claim 11, wherein the N-terminal end of either peptide is modified by the presence of a protecting group, which is selected from the group consisting of an acetyl group, a fluorenyl methoxy carbonyl group, a formyl group, a palmitoyl group, a myristyl group, a stearyl group, and polyethylene glycol (PEG).

13. A method for treating diabetes comprising:
administering a pharmaceutical composition comprising at least one peptide selected from a peptide consisting of the amino acid sequence of SEQ ID NO: 1 and a peptide consisting of the amino acid sequence of SEQ ID NO: 2, as an active ingredient, wherein the C-terminal end of either peptide is optionally modified by the presence of an amino group, or an azide group, and the N-terminal end of either peptide is optionally modified by the presence of a protecting group.

14. The method of claim 13, wherein the C-terminal end of either peptide is modified by the presence of an amino group, or an azide group, or the N-terminal end of either peptide is modified by the presence of a protecting group.

15. The method of claim 14, wherein the N-terminal end of either peptide is modified by the presence of a protecting group, which is selected from the group consisting of an acetyl group, a fluorenyl methoxy carbonyl group, a formyl group, a palmitoyl group, a myristyl group, a stearyl group, and polyethylene glycol (PEG).

* * * * *